(12) United States Patent
Martin

(10) Patent No.: US 11,135,158 B2
(45) Date of Patent: Oct. 5, 2021

(54) MEDICATED HARD CANDY PRODUCT FOR TREATING ESOPHAGEAL INFLAMMATION AND A METHOD USING THE SAME

(71) Applicant: Michael Lee Martin, Farmersville, OH (US)

(72) Inventor: Michael Lee Martin, Farmersville, OH (US)

( * ) Notice: Subject to any disclaimer, the term of this patent is extended or adjusted under 35 U.S.C. 154(b) by 0 days.

(21) Appl. No.: 16/159,564

(22) Filed: Oct. 12, 2018

(65) Prior Publication Data

US 2019/0060226 A1 Feb. 28, 2019

Related U.S. Application Data

(63) Continuation-in-part of application No. 14/720,918, filed on May 25, 2015, now abandoned.

(60) Provisional application No. 62/002,954, filed on May 26, 2014.

(51) Int. Cl.
*A61K 9/00* (2006.01)
*A61K 31/573* (2006.01)
*A61P 29/00* (2006.01)

(52) U.S. Cl.
CPC .......... *A61K 9/0056* (2013.01); *A61K 31/573* (2013.01); *A61P 29/00* (2018.01)

(58) Field of Classification Search
CPC ....... A61K 31/573; A61K 31/58; A61K 31/56
See application file for complete search history.

(56) References Cited

U.S. PATENT DOCUMENTS

| | | |
|---|---|---|
| D323,417 S | 1/1992 | Cacia |
| H001228 H | 9/1993 | Doering |
| 5,658,956 A | 8/1997 | Martin et al. |
| 5,674,912 A | 10/1997 | Martin |
| 5,762,963 A | 6/1998 | Byas-Smith |
| 5,827,527 A | 10/1998 | Leonard |
| 8,324,192 B2 | 12/2012 | Dohil et al. |
| 8,497,258 B2 | 7/2013 | Dohil et al. |
| 8,545,537 B2 | 10/2013 | Murphy Matro |
| 8,679,545 B2 | 3/2014 | Dohil et al. |
| 2004/0018242 A1* | 1/2004 | Cunningham ......... A61K 9/145 424/489 |
| 2004/0253307 A1 | 12/2004 | Hague et al. |
| 2006/0140989 A1 | 6/2006 | Harris et al. |
| 2007/0111978 A1 | 5/2007 | Dohil et al. |
| 2007/0149466 A1 | 6/2007 | Milburn et al. |
| 2009/0191275 A1 | 7/2009 | Dohil et al. |
| 2012/0258058 A1 | 10/2012 | Herrmann et al. |
| 2013/0096096 A1 | 4/2013 | Dohil et al. |
| 2014/0371179 A1 | 12/2014 | Simmons |

FOREIGN PATENT DOCUMENTS

WO 2000010528 A1 3/2000

OTHER PUBLICATIONS

Schroeder, Shauna et al., "Recent advances in the treatment of eosinophilic esophagitis", Expert Rev Clin Immunol. Nov. 2010; 6(6), pp. 1-15.
Kelly, Kevin J. et al., "Eosinophilic esophagitis attributed to gastroesophageal reflux: Improvement with an amino acid-based formula", Gastroenterology, Nov. 1995, vol. 109, Issue 5, pp. 1503-1512.
PCT Form 210, International Search Report for PCT/US2015/032349, dated Aug. 5, 2015.
PCT Form 237, Written Opinion of the International Searching Authority for PCT/US2015/032349, dated Aug. 5, 2015.

* cited by examiner

*Primary Examiner* — Dennis Heyer
(74) *Attorney, Agent, or Firm* — The Law Office of Patrick F. O'Reilly III, LLC (57) ABSTRACT

A medicated hard candy product for treating eosinophilic esophagitis (EoE) is disclosed herein. The medicated hard candy product includes a hard candy base material, the hard candy base material forming a substantially rigid candy product after being heated and permitted to cool for a predetermined time period; and a corticosteroid, the corticosteroid being intermixed with the hard candy base material. The medicated hard candy product is configured to reduce or alleviate esophageal inflammation and/or symptoms associated therewith in an individual when orally administered thereto. In one or more embodiments, the corticosteroid comprises one of: (i) budesonide, (ii) fluticasone, (iii) ciclesonide, (iv) beclomethasone dipropionate, and (v) mometasone furoate. Also, in one or more embodiments, the medicated hard candy product is in the form of a lollipop or lozenge. A method of treating, reducing, or alleviating esophageal inflammation in an individual, which utilizes the medicated hard candy product, is also disclosed herein.

17 Claims, 10 Drawing Sheets

SECTION A-A

SECTION B-B

SECTION C-C
FIG. 14

SECTION D-D

MEDICATED HARD CANDY PRODUCT FOR TREATING ESOPHAGEAL INFLAMMATION AND A METHOD USING THE SAME

CROSS-REFERENCE TO RELATED APPLICATIONS

This is a continuation-in-part of U.S. patent application Ser. No. 14/720,918, entitled "Medicated Hard Candy Product For Treating Esophageal Inflammation And A Method Using The Same", filed on May 25, 2015, and further claims the benefit of U.S. Provisional Patent Application No. 62/002,954, entitled "Medicated Hard Candy Product For Treating Esophageal Inflammation And A Method Using The Same", filed on May 26, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a medicated hard candy product. More particularly, the invention relates to a medicated hard candy product for treating esophageal inflammation and a method using the same.

2. Background

Eosinophilic esophagitis (EoE) is an allergic inflammatory condition of the esophagus that involves eosinophiles, a type of white blood cell. The typical symptoms of eosinophilic esophagitis (EoE) are difficulty swallowing, food impaction, and heartburn. Presently, there is no cure for eosinophilic esophagitis (EoE). One of the limited ways of treating eosinophilic esophagitis is with an elemental diet, or by removing allergenic foods. The dietary management approach is very challenging for the patient, and is often met with great resistance in adults and children alike. At this time, the overall treatment goal for eosinophilic esophagitis is to prevent the damaging inflammation that occurs due to migration of eosinophiles into the esophagus. If eosinophilic esophagitis is left untreated, the patient will gradually lose the ability to swallow, and eventually will be forced onto a feeding tube in order to survive.

Therefore, what is needed is a medicated hard candy product for treating esophageal inflammation that effectively treats eosinophilic esophagitis without subjecting the patient to the unpleasant limitations of an elemental diet. Moreover, a medicated hard candy product is needed that sufficiently coats substantially the full length of the peripheral wall of the esophagus so as to effectively treat eosinophilic esophagitis throughout the entire esophagus. Furthermore, there is a need for a medicated hard candy product that effectively treats eosinophilic esophagitis without a significant portion of the swallowed medicated product being wasted by failing to contact the esophagus wall. In addition, there is a need for a treatment method using a medicated hard candy product that has the abovementioned attributes.

BRIEF SUMMARY OF EMBODIMENTS OF THE INVENTION

Accordingly, the present invention is directed to a medicated hard candy product for treating esophageal inflammation and a method using the same that substantially obviates one or more problems resulting from the limitations and deficiencies of the related art.

In accordance with one or more embodiments of the present invention, there is provided a medicated hard candy product that includes a hard candy base material, the hard candy base material forming a substantially rigid candy product after being heated and permitted to cool for a predetermined time period; and a corticosteroid, the corticosteroid being intermixed with the hard candy base material. The medicated hard candy product is configured to reduce or alleviate esophageal inflammation or symptoms associated therewith in an individual when orally administered thereto.

In a further embodiment of the present invention, the hard candy base material comprises a sugar-free dry powder base prior to being heated.

In yet a further embodiment, the corticosteroid comprises one of: (i) budesonide, (ii) fluticasone, (iii) ciclesonide, (iv) beclomethasone dipropionate, and (v) mometasone furoate.

In still a further embodiment, the medicated hard candy product comprises between approximately 0.25 milligrams and approximately 1.0 milligrams of the corticosteroid.

In yet a further embodiment, the medicated hard candy product contains no water after being heated and permitted to cool for the predetermined time period.

In still a further embodiment, no water is used in the process of making the medicated hard candy product.

In yet a further embodiment, the medicated hard candy product is in the form of a lollipop or sucker.

In still a further embodiment, the medicated hard candy product is in the form of a lozenge.

In accordance with one or more other embodiments of the present invention, there is provided a medicated hard candy product that includes a hard candy base material, the hard candy base material forming a substantially rigid candy product after being heated and permitted to cool for a predetermined time period; and a corticosteroid, the corticosteroid being intermixed with the hard candy base material, the corticosteroid comprising one of: (i) budesonide, (ii) fluticasone, (iii) ciclesonide, (iv) beclomethasone dipropionate, and (v) mometasone furoate. The medicated hard candy product is configured to reduce or alleviate esophageal inflammation or symptoms associated therewith in an individual when orally administered thereto; and the medicated hard candy product is in the form of a lollipop or a lozenge.

In a further embodiment of the present invention, the hard candy base material comprises a sugar-free dry powder base prior to being heated.

In yet a further embodiment, the medicated hard candy product contains no water after being heated and permitted to cool for the predetermined time period.

In still a further embodiment, no water is used in the process of making the medicated hard candy product.

In yet a further embodiment, the medicated hard candy product is in the form of a lollipop.

In still a further embodiment, the medicated hard candy product is in the form of a lozenge.

In accordance with yet one or more other embodiments of the present invention, there is provided a method of treating, reducing, or alleviating esophageal inflammation in an individual comprising orally administering to the individual a medicated hard candy product, the medicated hard candy product comprising a hard candy base material, the hard candy base material forming a substantially rigid candy product after being heated and permitted to cool for a predetermined time period; and a corticosteroid, the corticosteroid being intermixed with the hard candy base material, the corticosteroid comprising one of: (i) budesonide, (ii) fluticasone, (iii) ciclesonide, (iv) beclomethasone dipropionate, and (v) mometasone furoate.

In a further embodiment of the present invention, the hard candy base material comprises a sugar-free dry powder base prior to being heated.

In yet a further embodiment, the medicated hard candy product contains no water after being heated and permitted to cool for the predetermined time period.

In still a further embodiment, no water is used in the process of making the medicated hard candy product.

In yet a further embodiment, the medicated hard candy product is in the form of a lollipop or sucker.

In still a further embodiment, the medicated hard candy product is in the form of a lozenge.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL
VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS
OF THE INVENTION

In one or more embodiments of the present invention, an orally-administered medicated hard candy product is provided that reduces or alleviates esophageal inflammation and/or symptoms associated therewith in an individual when orally administered thereto. In particular, the medicated hard candy reduces or alleviates esophageal inflammation that is caused by eosinophilic esophagitis (EoE). The medicated hard candy product generally comprises a hard candy base material, the hard candy base material forming a rigid or substantially rigid candy product after being heated and permitted to cool for a predetermined time period; and a corticosteroid, the corticosteroid being intermixed with the hard candy base material. The corticosteroid may comprise budesonide, fluticasone, ciclesonide, beclomethasone dipropionate, mometasone furoate, or another type of corticosteroid suitable for reducing or alleviating esophageal inflammation.

The hard candy base material of the medicated hard candy product may comprise a sugar-free dry powder base that is suitable for preparing hand candy that can be orally administered and absorbed across the sublingual or buccal mucosa. In one or more embodiments, the hard candy base material may have a very low hygroscopicity, bitterness masking, and a low caloric value. The hard candy base material may also be non-cariogenic such that it does not promote tooth decay of the patient. For example, the hard candy base material may comprise Lollibase® as manufactured by Fagron Group BV.

In order to make the medicated hard candy product more palatable to the patient, the medicated hard candy product may also include flavoring and sweeteners (e.g., sugar or a sugar substitute). For example, in one or more embodiments, the hard candy product may have a peppermint flavor or a fruit flavor (e.g., cherry flavor). Also, in order to make the medicated hard candy product more visually appealing to the patient, colors may be added to the hard candy mixture (e.g., the hard candy could be red, green, blue, or any other color that is desired).

Figure 1:
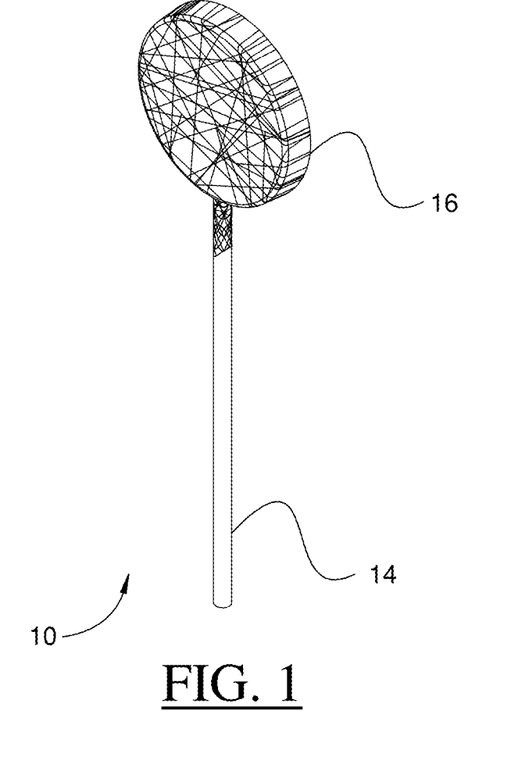
FIG. 1 is a perspective view of a medicated lollipop for treating esophageal inflammation, according to an embodiment of the invention, wherein the lollipop is illustrated with the wrapper thereon.
Figure 2:
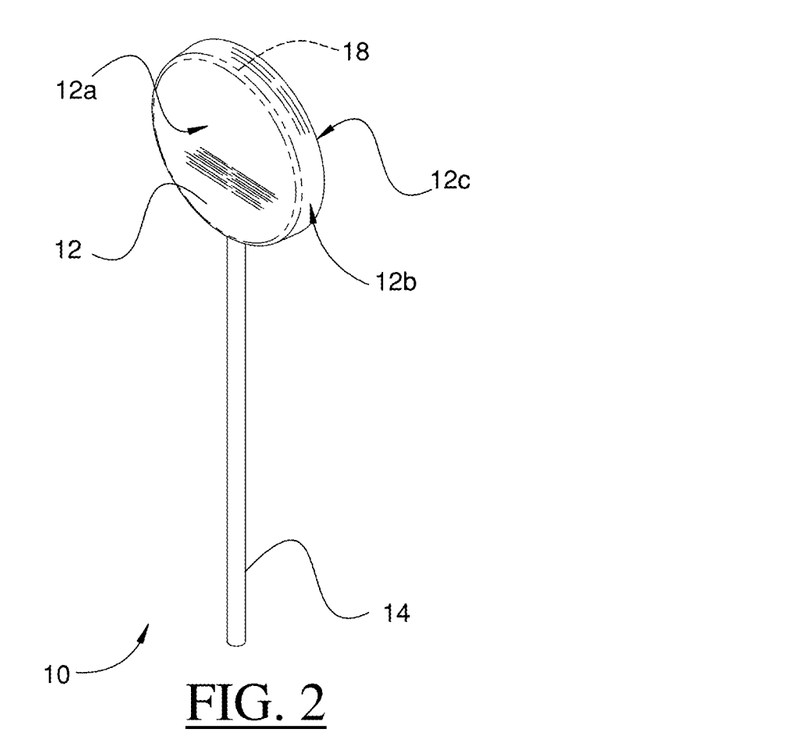
FIG. 2 is another perspective view of the medicated lollipop of FIG. 1, wherein the lollipop is illustrated with the wrapper removed therefrom.

In a first illustrative embodiment, the medicated hard candy product is in the form of a medicated lollipop or sucker 10. With reference to FIGS. 1-8, it can be seen that the medicated lollipop 10 generally comprises lollipop body portion 12 disposed on a stick member 14. The stick member 14 is embedded into the lollipop body portion 12 and serves as a handle for the user of the medicated lollipop 10 (see FIG. 8). Also, as shown in FIG. 1, the lollipop body portion 12 may comprise a foil wrapper 16 disposed therearound for hygienic purposes. When the user or patient is ready to consume the medicated lollipop 10, he or she simply removes the foil wrapper 16 from the lollipop body portion 12.

Figure 3:
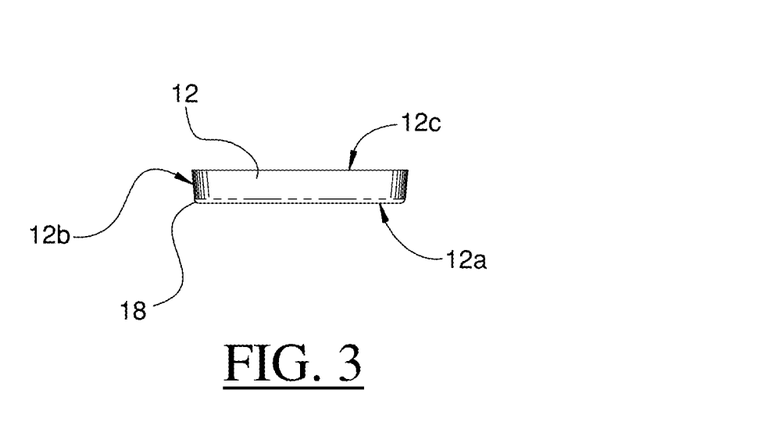
FIG. 3 is a top view of the medicated lollipop of FIG. 2.
Figure 4:
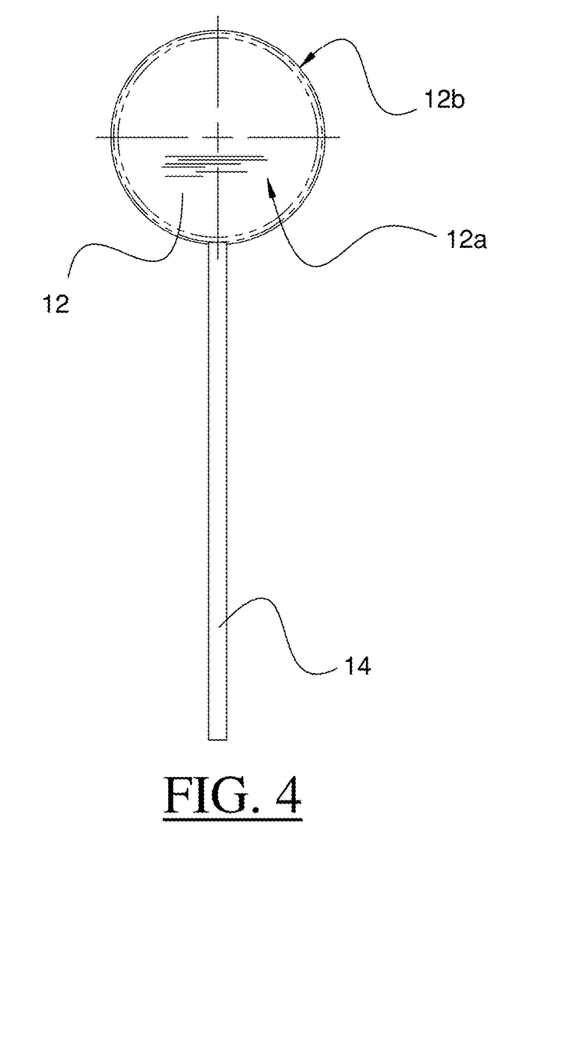
FIG. 4 is a front view of the medicated lollipop of FIG. 2.
Figure 5:
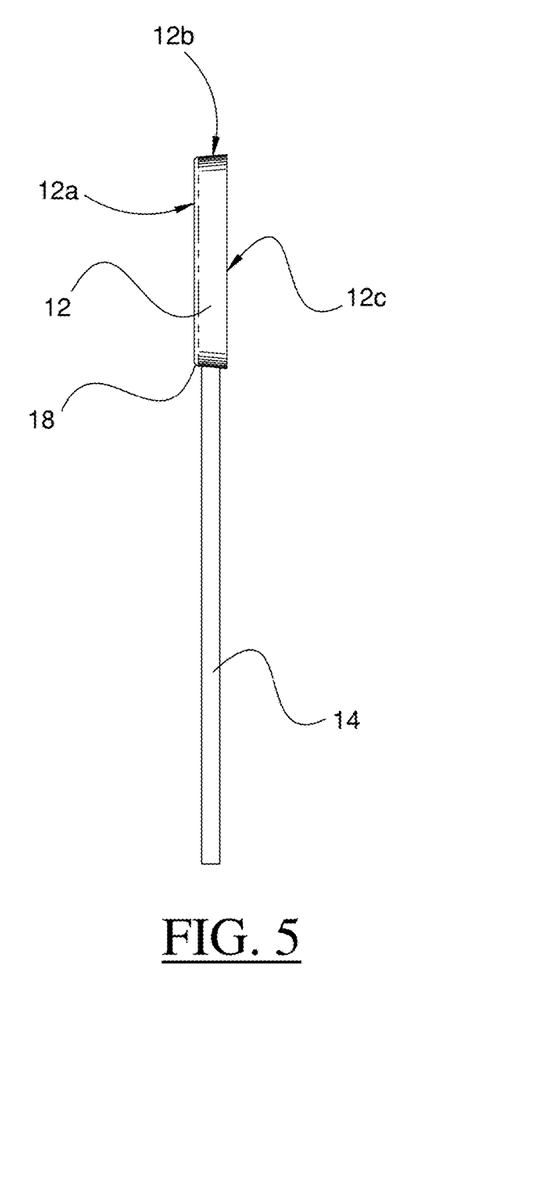
FIG. 5 is a side view of the medicated lollipop of FIG. 2.
Figure 6:
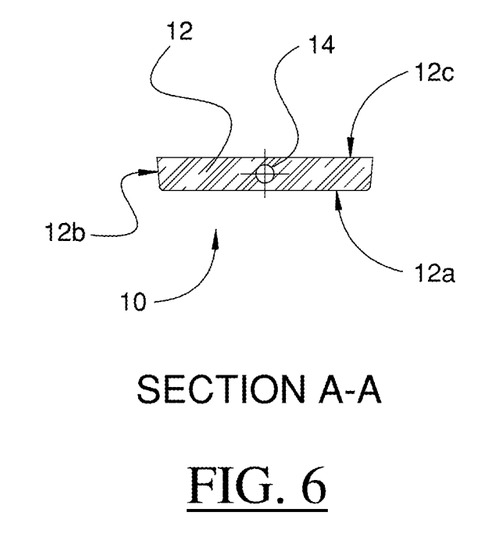
FIG. 6 is a transverse sectional view of the medicated lollipop of FIG. 2, wherein the section is cut along the cutting plane line A-A in FIG. 7.
Figure 7:
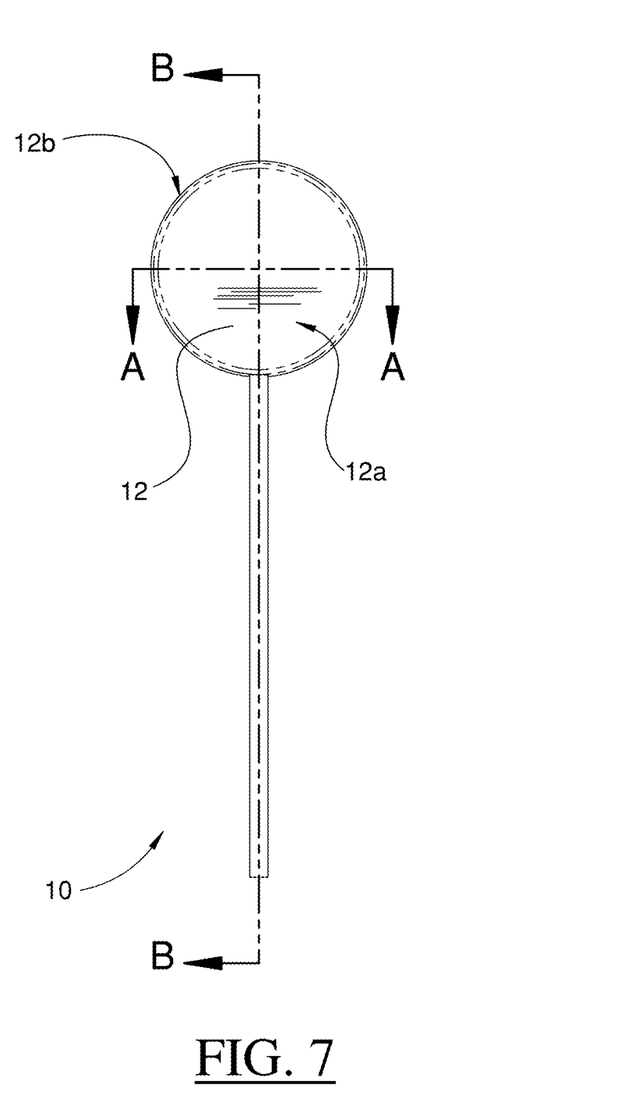
FIG. 7 is another front view of the medicated lollipop of FIG. 2, wherein the section cut lines are illustrated thereon.
Figure 8:
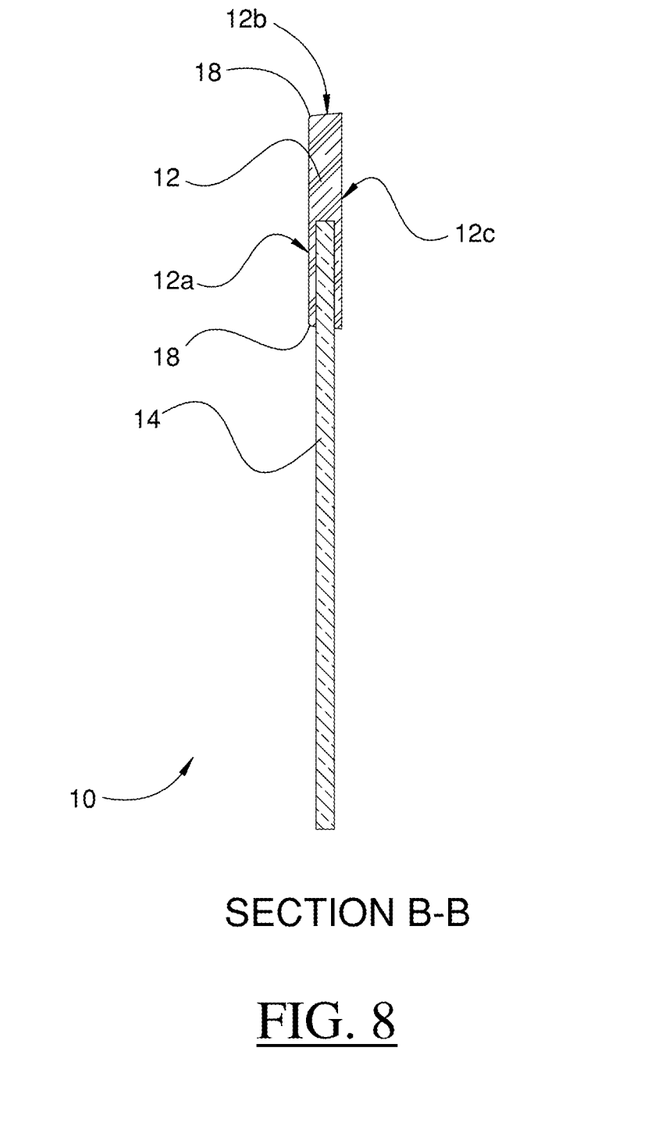
FIG. 8 is a longitudinal sectional view of the medicated lollipop of FIG. 2, wherein the section is cut along the cutting plane line B-B in FIG. 7.

Now, referring to FIGS. 2-7, the structure of the lollipop body portion 12 will be described in more detail. As shown in these figures, it can be seen that the lollipop body portion 12 comprises a generally planar front surface 12a, a tapered circular side surface 12b, and a generally planar rear surface 12c. As best shown in FIGS. 3 and 6, the front surface 12a is disposed generally parallel to the rear surface 12c. Also, with reference to FIGS. 3 and 5, it can be seen that the lollipop body portion 12 is provided with a rounded front peripheral edge 18. In FIG. 3, it can be seen that the rounded front peripheral edge 18 is provided at the location where the front surface 12a adjoins the tapered circular side surface 12b. Advantageously, the rounded front peripheral edge 18 of the lollipop body portion 12 substantially minimizes the risk that a user of the medicated lollipop 10 will inadvertently cut his or her tongue on a sharp edge of the lollipop body portion 12.

Figure 9:
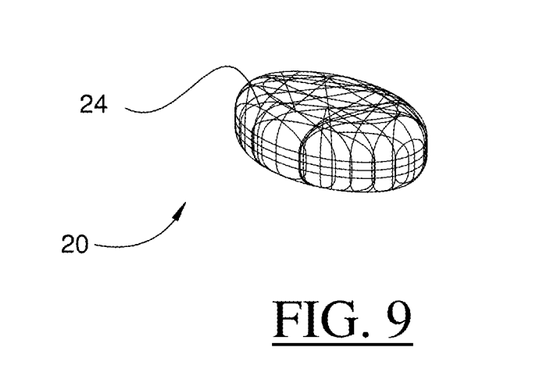
FIG. 9 is a perspective view of a medicated lozenge for treating esophageal inflammation, according to an embodiment of the invention, wherein the lozenge is illustrated with the wrapper thereon.
Figure 10:
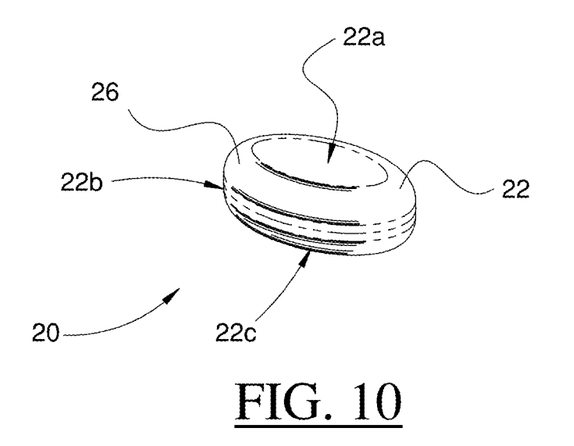
FIG. 10 is another perspective view of the medicated lozenge of FIG. 9, wherein the lozenge is illustrated with the wrapper removed therefrom.
Figure 11:
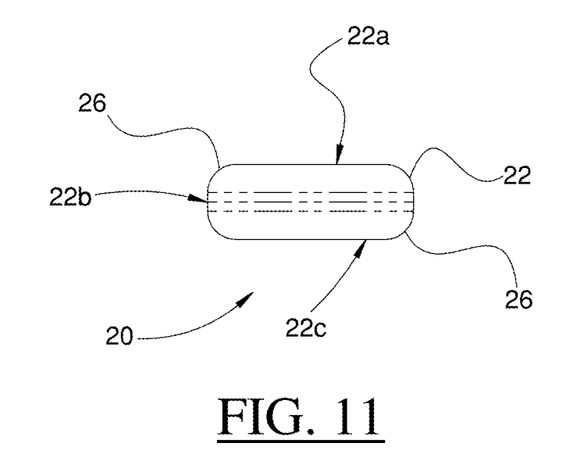
FIG. 11 is a side view of the medicated lozenge of FIG. 10.
Figure 12:
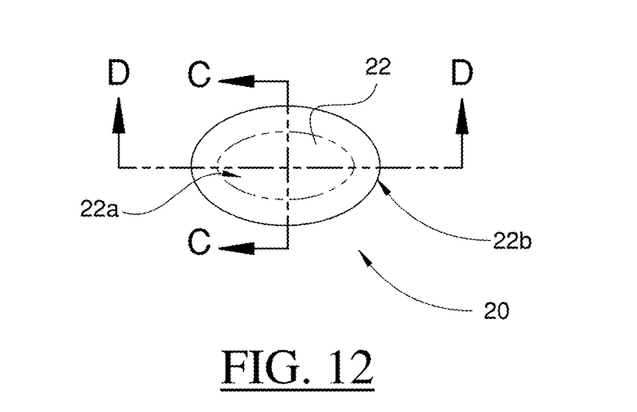
FIG. 12 is a top view of the medicated lozenge of FIG. 10, wherein the section cut lines are illustrated thereon.
Figure 13:
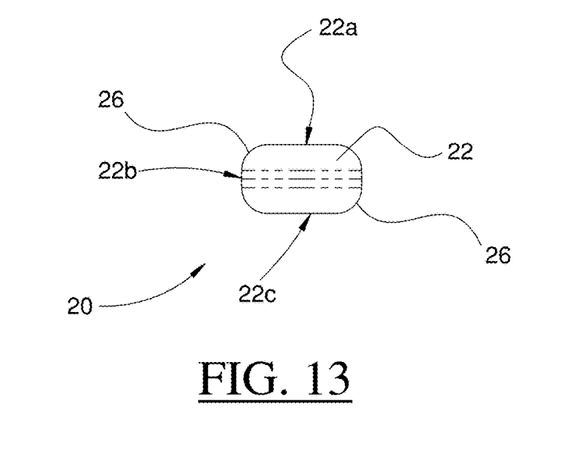
FIG. 13 is an end view of the medicated lozenge of FIG. 10.
Figure 14:
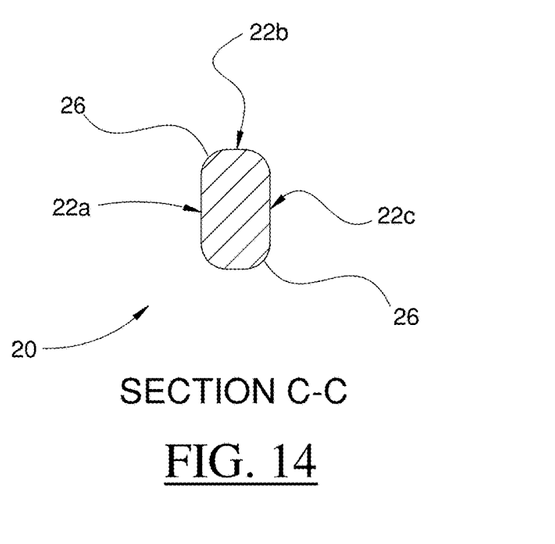
FIG. 14 is a transverse sectional view of the medicated lozenge of FIG. 10, wherein the section is cut along the cutting plane line C-C in FIG. 12.
Figure 15:
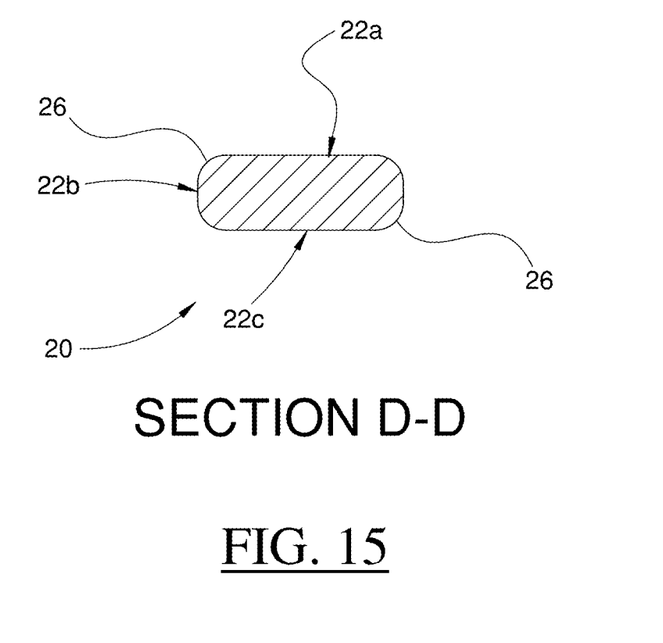
FIG. 15 is a longitudinal sectional view of the medicated lozenge of FIG. 10, wherein the section is cut along the cutting plane line D-D in FIG. 12.

In a second illustrative embodiment, the medicated hard candy product is in the form of a medicated lozenge 20. With reference to FIGS. 9-15, it can be seen that the medicated lozenge 20 generally comprises an ellipsoidal body portion 22 with flattened top and bottom surfaces. As shown in FIG. 9, similar to the lollipop body portion 12, the lozenge body portion 22 may comprise a foil wrapper 24 disposed therearound for hygienic purposes. When the user or patient is ready to consume the medicated lozenge 20, he or she simply removes the foil wrapper 24 from the lozenge body portion 22.

Now, referring to FIGS. 10-15, the structure of the lozenge body portion 22 will be described in more detail. As shown in these figures, it can be seen that the lozenge body portion 22 comprises a generally planar front surface 22a, a curved side surface 22b, and a generally planar rear surface 22c. As best shown in FIGS. 11 and 13-15, the front surface 22a is disposed generally parallel to the rear surface 22c. Also, with reference again to FIGS. 11 and 13-15, it can be seen that the lozenge body portion 22 is provided with a rounded peripheral edges 26 circumscribing the front and rear edges thereof. As shown in these figures, it can be seen that the rounded peripheral edges 26 are provided at the location where the front surface 22a adjoins the curved side surface 22b and at the location where the rear surface 22c adjoins the curved side surface 22b. Advantageously, the rounded peripheral edges 26 of the lozenge body portion 22 substantially minimize the risk that a user of the medicated lozenge 20 will inadvertently cut his or her tongue on a sharp edge of the lozenge body portion 22.

In one or more embodiments, the medicated hard candy product (e.g., the lollipop 10 or the lozenge 20) may comprise between approximately 0.1 milligrams and approximately 2.0 milligrams of the corticosteroid (e.g., budesonide), or between 0.1 milligrams and 2.0 milligrams of the corticosteroid (e.g., budesonide). More preferably, in one or more embodiments, the medicated hard candy product (e.g., the lollipop 10 or the lozenge 20) may comprise between approximately 0.25 milligrams and approximately 1.0 milligrams of the corticosteroid (e.g., budesonide), or between 0.25 milligrams and 1.0 milligrams of the corticosteroid (e.g., budesonide). Still even more preferably, in one or more embodiments, the medicated hard candy product (e.g., the lollipop 10 or the lozenge 20) may comprise approximately 0.5 milligrams of the corticosteroid (e.g., budesonide), or 0.5 milligrams of the corticosteroid (e.g., budesonide). The amounts (in units of mass) of the corticosteroid in these embodiments have been determined such that the amount of the corticosteroid is sufficient to effectively reduce or alleviate esophageal inflammation and/or the symptoms associated therewith in an individual caused by eosinophilic esophagitis (EoE), yet not result in an excessive amount of the corticosteroid being delivered to the individual, which may produce negative side effects therefrom. In general, when ranges of a particular substance (e.g., a corticosteroid) are specified in this disclosure, the ranges are inclusive of the values encompassed within the specified range and the upper and lower limit boundaries themselves (e.g., between 0.1 and 2.0 milligrams includes the milligram values between the lower limit of 0.1 milligrams and the upper limit of 2.0 milligrams, as well as the lower and upper limit values of 0.1 and 2.0 milligrams).

In one or more embodiments, when the medicated hard candy product is provided in the form of the medicated lollipop 10, the overall mass of the lollipop 10 may be between approximately 4.0 grams and approximately 17.0 grams (or between 4.0 grams and 17.0 grams). More preferably, in one or more embodiments, when the medicated hard candy product is provided in the form of the medicated lollipop 10, the overall mass of the lollipop 10 may be between approximately 6.5 grams and approximately 12.0 grams (or between 6.5 grams and 12.0 grams). Still even more preferably, in one or more embodiments, the overall mass of the lollipop 10 may be approximately 8.5 grams (or 8.5 grams). The overall masses of the lollipop 10 in these embodiments have been determined such that the lollipop 10 is capable of delivering a requisite amount of the corticosteroid, yet not be excessively large and difficult to consume.

In one exemplary embodiment, when the medicated hard candy product is provided in the form of the medicated lollipop 10, the medicated lollipop 10 has an overall mass with the stick member 14 of approximately 9.141 grams, and has an overall mass without the stick member 14 of approximately 8.437 grams. In this exemplary embodiment, the medicated lollipop 10 is provided with 1.0 milligram or 0.001 grams of budesonide, so that the medicated lollipop 10 contains approximately 0.0119 percent budesonide by weight (i.e., without considering the weight of the stick member 14). Also, in one or more other embodiments, the medicated lollipop 10 may contain at least 0.003 percent of the corticosteroid (e.g., budesonide) by weight (i.e., 0.25 milligrams of the corticosteroid in a medicated lollipop 10 weighing 8.5 grams without the stick member 14) so that the amount of the corticosteroid is sufficient to effectively reduce or alleviate esophageal inflammation and/or the symptoms associated esophageal inflammation in an individual caused by eosinophilic esophagitis (EoE).

In one or more further embodiments, the top end of the lollipop stick member 14 is coated with an anti-fungal medication. Advantageously, the anti-fungal medication on the top end of the lollipop stick member 14 treats oropharyngeal candidiasis (i.e., oral and esophageal thrush), which may be caused by the corticosteroid delivered by the medicated lollipop 10. As such, in this further embodiment, the patient initially consumes the lollipop body portion 12 that delivers the corticosteroid for treating eosinophilic esophagitis (EoE), and then the patient subsequently receives a predetermined dosage of the anti-fungal medication on the top end of the lollipop stick member 14, which has been exposed after the lollipop body portion 12 has been consumed, for treating the oropharyngeal candidiasis. This inventive two-step treatment method not only effectively treats eosinophilic esophagitis (EoE), but also effectively treats any oropharyngeal candidiasis resulting from the consumption of the corticosteroid in the lollipop 10. The anti-fungal medication applied to the top end of the lollipop stick member 14 may comprise nystatin, Diflucan, fluconazole, Mycelex Troche, clotrimazole, Mycostatin, Nilstat, Bio-Statin, miconazole, ketoconazole, Amphocin, Sporanox PulsePak, Fungizone, gentian violet, itraconazole, amphotericin b, miconazole, Oravig, Sporanox, Noxafil, Onmel, and posaconazole, or another type of anti-fungal medication suitable for reducing or alleviating oral and/or esophageal thrush. In addition, similar to that described above for the hard candy product, the top end of the lollipop stick member 14 may have a peppermint flavor or a fruit flavor (e.g., a cherry flavor) to make the unpleasant flavor (e.g., bitter flavor) of the anti-fungal medication more tolerable for the patient.

In one exemplary embodiment, the anti-fungal medication applied to the top end of the lollipop stick member 14 is nystatin. Nystatin is not absorbed into the bloodstream of the patient. In this exemplary embodiment, the dosage of nystatin provided on the lollipop stick member 14 is functionally equivalent to 400,000 to 600,000 international units (IU) in an oral suspension form. In this exemplary embodiment, this dosage is administered to the patient four times per day.

Now, a first exemplary procedure for making the medicated lollipop 10 will be described in detail. First of all, the necessary quantities (e.g., percentage amounts) of each of the requisite ingredients for the medicated lollipop 10 are determined (i.e., calculated) and procured. Of course, these prescribed quantities of ingredients are dependent upon the lollipop batch size that is to be made. In particular, a predetermined quantity of the following ingredients will be prepared for the batch of medicated lollipops 10: (i) a predetermined quantity of a corticosteroid (e.g., budesonide), (ii) a predetermined quantity of water, and (iii) a predetermined quantity of the hard candy base material (e.g., Lollibase®). Also, optionally, if the user or patient wants the medicated lollipops 10 to be flavored, a flavoring substance (e.g., peppermint or a fruit flavor) may also be added as an ingredient in the mixture. Similarly, if the medicated lollipops 10 are to be formed having a specific color, a coloring substance may also be added as another optional ingredient in the mixture.

Once the necessary ingredients are procured, the next step in the exemplary procedure is to add the hard candy base material and the water into a suitable beaker. Then, the solution of the hard candy base material and the water are heated or "cooked" using a suitable heating device (e.g., a hotplate). Next, when the solution reaches a temperature of approximately 148 degrees Celsius (298.4 degrees Fahrenheit), the beaker with the solution of the hard candy base material and water are removed from the heating device (e.g., a hotplate). Then, the corticosteroid (e.g., budesonide) and the optional flavoring are quickly added to the solution, and the solution is stirred so as to adequately mix the constituent ingredients. After stirring the ingredients together, the solution is poured into lollipop or sucker molds that form the shape of the medicated lollipops 10. Prior to pouring the solution into the molds, the lollipop molds are basted with a non-sticking substance (e.g., canola oil) and the lollipop sticks 14 are properly positioned in the molds. If the solution begins to solidify or harden before it is completely poured into all of the lollipop molds, it may be necessary to reheat the solution, and then finish the pouring thereof into the molds. Finally, after being poured into the molds, the lollipops are allowed to cool and solidify for a predetermined time period (e.g., for a duration of at least two (2) hours) before they are wrapped with the wrappers 16. It is to be understood that a similar procedure to that described above may be used for forming the medicated lozenges 20, except that no sticks 14 will be necessary and the molds utilized will form the shape of the lozenge body portion 22, rather than the shape of the lollipop body portion 12.

Even though water is used in the first exemplary procedure for making the medicated lollipop 10, the final medicated hard candy product (e.g., the medicated lollipop 10) contains no residual water therein because all of the water is boiled off when the solution is heated to a temperature of approximately 148 degrees Celsius (298.4 degrees Fahrenheit).

Next, a second exemplary procedure for making the medicated lollipop 10 will be described in detail. The second exemplary procedure for making the medicated lollipop 10 is similar in most respects to the first exemplary procedure described above, except that no water is used in the process of making the medicated lollipop 10. Initially, the necessary quantities (e.g., percentage amounts) of each of the requisite ingredients for the medicated lollipop 10 are determined (i.e., calculated) and procured. Of course, these prescribed quantities of ingredients are dependent upon the lollipop batch size that is to be made. In particular, a predetermined quantity of the following ingredients will be prepared for the batch of medicated lollipops 10: (i) a predetermined quantity of a corticosteroid (e.g., budesonide) and (ii) a predetermined quantity of the hard candy base material (e.g., Lollibase®). Also, optionally, if the user or patient wants the medicated lollipops 10 to be flavored, a flavoring substance (e.g., peppermint or a fruit flavor) may also be added as an ingredient in the mixture. Similarly, if the medicated lollipops 10 are to be formed having a specific color, a coloring substance may also be added as another optional ingredient in the mixture.

Once the necessary ingredients are procured, the next step in the second exemplary procedure is to fill a suitable beaker with the hard candy base material. Then, the hard candy base material in the beaker is heated or "cooked" using a suitable heating device (e.g., a hotplate). Next, when the hard candy base material liquefies and reaches a temperature of approximately 148 degrees Celsius (298.4 degrees Fahrenheit), the beaker with the liquefied hard candy base material is removed from the heating device (e.g., a hotplate). Then, the corticosteroid (e.g., budesonide) and the optional flavoring are quickly added to the liquefied hard candy base material, and the solution is stirred so as to adequately mix the constituent ingredients. After stirring the ingredients together, the solution is poured into lollipop or sucker molds that form the shape of the medicated lollipops 10. Prior to pouring the solution into the molds, the lollipop molds are basted with a non-sticking substance (e.g., canola oil) and the lollipop sticks 14 are properly positioned in the molds. If the solution begins to solidify or harden before it is completely poured into all of the lollipop molds, it may be necessary to reheat the solution, and then finish the pouring thereof into the molds. Finally, after being poured into the molds, the lollipops are allowed to cool and solidify for a predetermined time period (e.g., for a duration of at least two (2) hours) before they are wrapped with the wrappers 16. It is to be understood that a similar procedure to that described above may be used for forming the medicated lozenges 20, except that no sticks 14 will be necessary and the molds utilized will form the shape of the lozenge body portion 22, rather than the shape of the lollipop body portion 12.

In the further embodiment described above, when the top end of the lollipop stick member 14 is coated with an anti-fungal medication, the top ends of the lollipop sticks 14 are initially coated with the anti-fungal medication (i.e., in stage one), and then the lollipop sticks 14 are subsequently positioned in the molds so that the solution containing the corticosteroid and the hard candy base material is able to solidify on the lollipop sticks 14 (i.e., in stage two).

Advantageously, when no water is used in the process of making the medicated lollipop 10, the shelf life of the medicated lollipop 10 is increased from 30 days (i.e., when water is used in the process) to a shelf life of 6 months (i.e., when no water is used in the process).

In one or more embodiments, the hard candy base material (i.e., lollipop base material) used in the above described procedure is gluten-free, citric acid free, and sugar free. In these one or more embodiments, the hard candy base material generally comprises a blend or mixture of sugar alcohols (i.e., polyalcohols) from natural sources. Because the hard candy base material is a polyalcohol, it turns into a liquid when boiled. Also, in these one or more embodiments, the hard candy base material does not promote tooth decay. As described above in the exemplary procedure, the other main ingredients utilized in the process of making the lollipops, other than water, are a corticosteroid in the form of budesonide, pure canola oil to prevent the lollipops from sticking to the mold(s), and the optional natural flavor or flavors (e.g., peppermint). As alternative to, or in addition to peppermint flavoring, the following other natural flavors may be utilized in the solution used for making the medicated lollipops 10: almond, banana, blueberry, cherry, chocolate, cranberry, cinnamon, caramel, maple, pomegranate, raspberry, strawberry, toffee, licorice, lemon, orange, grapefruit, key lime, lime, pear, spearmint, tangerine, and wintergreen.

Now, the results of an effective treatment procedure for alleviating the symptoms of Eosinophilic Esophagitis (EoE) that was performed using the above described medicated lollipops 10 will be explained in detail. The treatment procedure was performed on the EoE patient for a time duration of approximately six (6) weeks. During each day of treatment, the patient orally ingested two (2) medicated lollipops 10. Each of the medicated lollipops 10 contained approximately 0.5 milligrams (MG) of budesonide. As such, the dosage of medication (budesonide) that the patient received during the treatment procedure was generally 0.5 MG BID (i.e., twice per day). The shelf life of the medicated lollipops 10 that were used during the treatment was approximately six (6) months. Also, the medicated lollipops 10 that were used during the treatment were peppermint-flavored, but because the flavoring is in no way connected to the medication itself, it is readily apparent that other flavors, or medicated lollipops 10 with no flavoring would have the same result as the lollipops 10 used in this treatment procedure. In addition, the medicated lollipops 10 that were used during the treatment were clear (i.e., they had no coloring added thereto), but because the coloring, like the flavoring, is in no way connected to the medication itself, it is readily apparent that medicated lollipops 10 having a particular color (e.g., red, green, blue, etc.) would have the same result as the lollipops 10 used in this treatment procedure.

During the treatment, the patent typically consumed each medicated lollipop 10 in approximately 15-20 minutes (or between 15 and 20 minutes, inclusive). After consuming each of the medicated lollipops 10, the patient did not orally ingest any other food or drink items for at least one-half (½) hour after the consumption of each medicated lollipop 10.

An upper endoscopy image of the patient's esophagus was taken before and after the treatment with the medicated lollipops 10. Before treatment, the peripheral wall of the patient's esophagus contained white exudates with numerous eosinophiles, as well as ridges, furrows, or rings on the esophagus wall. In stark contrast, a clear endoscopic image of the patient's esophagus was obtained following the above described treatment. The post-treatment upper/proximal endoscopic image revealed that the peripheral wall of the patient's esophagus was totally clear (i.e., it did not contain the white exudates comprising eosinophiles that were clearly present prior to the treatment). The post-treatment endoscopy performed on the patient revealed generally the same results for the distal esophagus (i.e., the portion of the esophagus closest to the stomach), namely that the distal esophagus also did not contain the white exudates comprising eosinophiles. In addition, biopsies that were performed on the patient in conjunction with the post-treatment upper endoscopy also confirmed the absence of eosinophiles. As such, the medicated lollipops 10 resulted in an endoscopic image illustrating an esophagus free of white exudates, whereas an elemental diet and very limited food intake failed to do so for this same patient. Consequently, it is readily apparent that the medicated lollipops 10 are an effective means by which to treat, reduce, and generally alleviate esophageal inflammation resulting from Eosinophilic Esophagitis (EoE) using a relatively low dosage of a corticosteroid (e.g., budesonide). Also, the treatment described herein, which used the medicated lollipops 10, resulted in a distal esophagus that was far more clean than that which is possible with the conventional methods that are used to treat Eosinophilic Esophagitis (EoE). Unlike the treatment procedure described herein, these conventional methods of EoE treatment are unable to heal the distal portion of the esophagus due to their lack of coverage in the distal areas of the esophagus.

Figure 16:
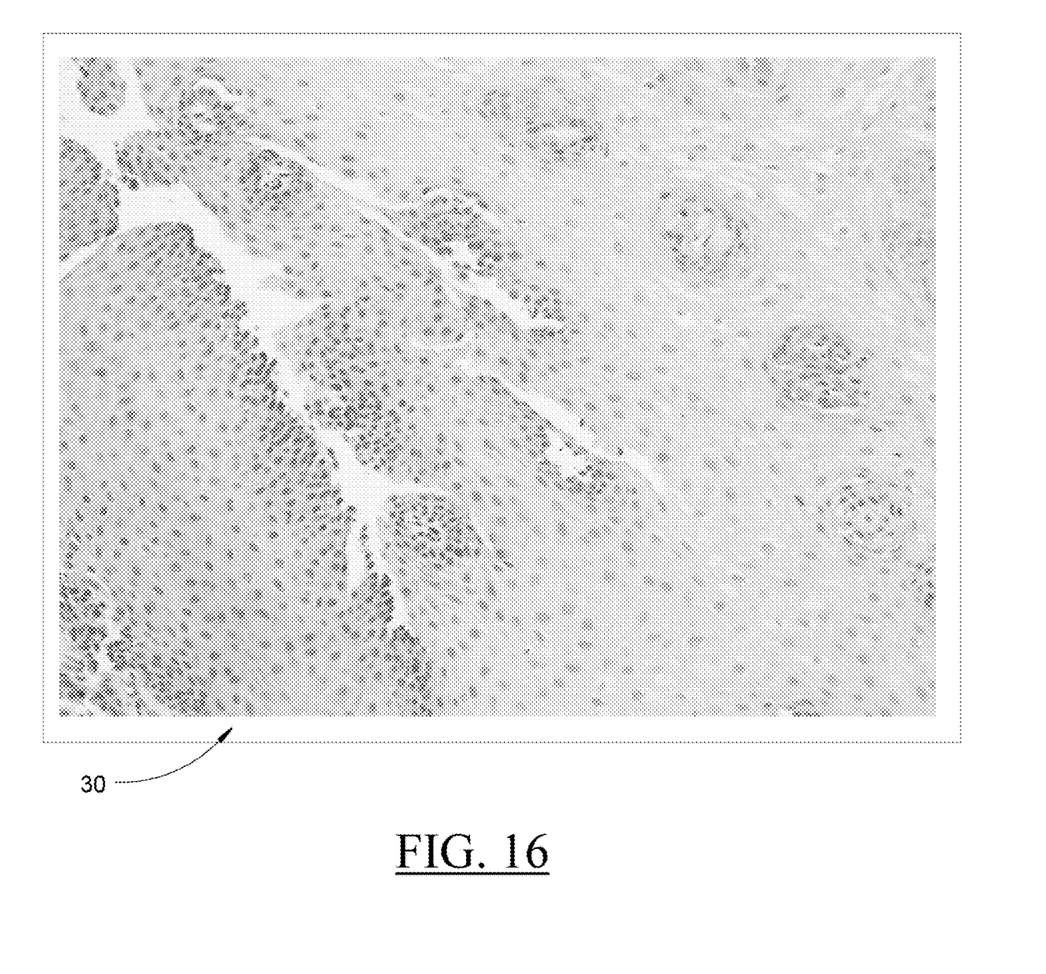
FIG. 16 illustrates a post-treatment biopsy slide for a patient that was treated using the medicated hard candy product of the present invention.

A post-treatment biopsy slide 30 of the patient's esophageal tissue is illustrated in FIG. 16. As shown in FIG. 16, after the patient ingested the medicated lollipops 10 over the six week time period, the basal cell layer of the patient's esophagus exhibited a normal cell structure. In the normal biopsy slide 30 of FIG. 16, there are no eosinophiles present. As such, the post-treatment biopsy slide 30 in this figure clearly demonstrates that the patient's Eosinophilic Esophagitis (EoE) was effectively treated by the consumption of the medicated lollipops 10 over the six week time period.

Advantageously, after the patient's doctor examined the clean endoscopic images, the patient was permitted to add additional types of food to his diet, which were not permitted prior to the treatment. This permitted addition of other foods to the patient's diet significantly improved the patient's quality of life because he was now permitted to enjoy other types of food without worrying about aggravating the symptoms associated with his Eosinophilic Esophagitis (EoE).

It is readily apparent that the aforedescribed medicated hard candy product 10, 20 offers numerous advantages. First, the medicated hard candy product 10, 20, and the treatment method using the same, effectively treats eosinophilic esophagitis without subjecting the patient to the unpleasant limitations of an elemental diet. Secondly, the medicated hard candy product 10, 20 sufficiently coats substantially the full length of the peripheral wall of the esophagus so as to effectively treat eosinophilic esophagitis throughout the entire esophagus. Finally, the medicated hard candy product 10, 20 effectively treats eosinophilic esophagitis without a significant portion of the swallowed medicated product being wasted by failing to contact the esophagus wall. That is, because only a small amount of the liquefied medicated candy product is swallowed by the patient at one time (e.g., as the lollipop or lozenge is gradually consumed by the patient), the medicated candy product generally flows down the esophagus wall without a significant portion being conveyed down the central portion of the esophagus, where it would just be wasted. As such, the medicated hard candy product described herein advantageously maximizes the time during which the corticosteroid in the product is in contact with the mucosal layer of the esophagus wall (i.e., it maximizes the contact time of the corticosteroid with the mucosal layer of the esophagus wall).

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of treating, reducing, or alleviating esophageal inflammation in an individual comprising orally administering to said individual a medicated hard candy product in a first stage and a second stage, said medicated hard candy product comprising:
    a hard candy base material, said hard candy base material forming a substantially rigid candy product after being heated and permitted to cool for a predetermined time period;
    a corticosteroid, said corticosteroid being intermixed with said hard candy base material, said corticosteroid comprising one of: (i) budesonide, (ii) fluticasone, (iii) ciclesonide, (iv) beclomethasone dipropionate, and (v) mometasone furoate, said corticosteroid being effective to treat esophageal inflammation and/or the symptoms associated therewith caused by eosinophilic esophagitis; and
    an anti-fungal medication, said anti-fungal medication being effective to treat oropharyngeal candidiasis caused by said corticosteroid, wherein said anti-fungal medication is nystatin;
    in the first stage, administering said corticosteroid for treating said eosinophilic esophagitis by said individual consuming a first portion of said medicated hard candy product comprising said corticosteroid; and
    in the second stage, administering said anti-fungal medication for treating oropharyngeal candidiasis caused by said corticosteroid by said individual consuming a second portion of said medicated hard candy product comprising said anti-fungal medication.

2. The method according to claim 1, wherein said hard candy base material comprises a sugar-free dry powder base prior to being heated.

3. The method according to claim 1, wherein said medicated hard candy product contains no water after being heated and permitted to cool for said predetermined time period.

4. The method according to claim 1, wherein no water is used in the process of making said medicated hard candy product, thereby substantially increasing a shelf life of said medicated hard candy product.

5. The method according to claim 4, wherein said shelf life of said medicated hard candy product is approximately 6 months.

6. The method according to claim 1, wherein said medicated hard candy product is in the form of a lollipop or sucker.

7. The method according to claim 1, wherein said medicated hard candy product comprises between approximately 0.25 milligrams and approximately 2.0 milligrams of said corticosteroid.

8. The method according to claim 7, wherein said medicated hard candy product comprises between approximately 0.25 milligrams and approximately 1.0 milligrams of said corticosteroid.

9. The method according to claim 1, wherein the overall mass of said medicated hard candy product is between approximately 4.0 grams and approximately 17.0 grams.

10. A method of treating, reducing, or alleviating esophageal inflammation in an individual comprising orally administering to said individual a medicated lollipop in a first stage and a second stage, said medicated lollipop comprising:
    a hard candy base material, said hard candy base material forming a substantially rigid lollipop body portion after being heated and permitted to cool for a predetermined time period;
    a corticosteroid, said corticosteroid being intermixed with said hard candy base material, wherein said corticosteroid is budesonide, said corticosteroid being effective to treat esophageal inflammation and/or the symptoms associated therewith caused by eosinophilic esophagitis; and
    a lollipop stick comprising an anti-fungal medication, said anti-fungal medication being effective to treat oropharyngeal candidiasis caused by said corticosteroid, said anti-fungal medication being coated on a top end of said lollipop stick, wherein said anti-fungal medication is nystatin;
    in the first stage, administering said corticosteroid for treating said eosinophilic esophagitis by said individual consuming said lollipop body portion; and
    in the second stage, administering said anti-fungal medication for treating oropharyngeal candidiasis caused by said corticosteroid by said individual consuming said anti-fungal medication coated on said top end of said lollipop stick.

11. The method according to claim 10, wherein said hard candy base material comprises a sugar-free dry powder base prior to being heated.

12. The method according to claim 10, wherein said medicated lollipop contains no water after being heated and permitted to cool for said predetermined time period.

13. The method according to claim 10, wherein no water is used in the process of making said medicated lollipop, thereby substantially increasing a shelf life of said medicated lollipop.

14. The method according to claim 13, wherein said shelf life of said medicated lollipop is approximately 6 months.

15. The method according to claim 10, wherein said medicated lollipop comprises between approximately 0.25 milligrams and approximately 2.0 milligrams of said corticosteroid.

16. The method according to claim 15, wherein said medicated lollipop comprises between approximately 0.25 milligrams and approximately 1.0 milligrams of said corticosteroid.

17. The method according to claim 10, wherein the overall mass of said medicated lollipop is between approximately 4.0 grams and approximately 17.0 grams.

* * * * *